(12) United States Patent
Sullivan

(10) Patent No.: US 8,965,501 B2
(45) Date of Patent: Feb. 24, 2015

(54) SEQUENTIAL STACKED CAPACITOR DEFIBRILLATOR AND WAVEFORM GENERATED THEREFROM

(71) Applicant: Physio-Control, Inc., Redmond, WA (US)

(72) Inventor: Joseph L. Sullivan, Kirkland, WA (US)

(*) Notice: Subject to any disclaimer, the term of this patent is extended or adjusted under 35 U.S.C. 154(b) by 0 days.

(21) Appl. No.: 13/962,934

(22) Filed: Aug. 8, 2013

(65) Prior Publication Data

US 2014/0046393 A1  Feb. 13, 2014

Related U.S. Application Data

(60) Provisional application No. 61/682,156, filed on Aug. 10, 2012.

(51) Int. Cl.
*A61N 1/00* (2006.01)
*A61N 1/39* (2006.01)

(52) U.S. Cl.
CPC ............... *A61N 1/3925* (2013.01); *A61N 1/39* (2013.01); *A61N 1/3912* (2013.01)
USPC .......................................................... 607/7

(58) Field of Classification Search
CPC ..... A61N 1/39; A61N 1/3925; A61N 1/3906; A61N 1/3912; A61N 1/3937
USPC .......................................................... 607/7
See application file for complete search history.

(56) References Cited

U.S. PATENT DOCUMENTS

| | | | |
|---|---|---|---|
| 5,111,813 A * | 5/1992 | Charbonnier et al. | 607/8 |
| 6,546,285 B1 | 4/2003 | Owen et al. | |
| 6,873,133 B1 | 3/2005 | Kavounas | |
| 6,954,669 B1 | 10/2005 | Fishler et al. | |
| 2003/0055460 A1 | 3/2003 | Owen et al. | |
| 2004/0172072 A1 * | 9/2004 | Brewer et al. | 607/8 |

OTHER PUBLICATIONS

Seidl, Karlheinz, MD, et al, Stepped Defibrillation Waveform is Substantially More Efficient than the 50/50% Titl Biphasic, Copyright 2006 Heart Rhythm Society.

* cited by examiner

*Primary Examiner* — George Manuel

(57) ABSTRACT

A medical device such as an external defibrillator delivers electrical therapy using a special ascending, biphasic waveform. The special waveform is characterized by a set of at least two peaks. The amplitude of the second peak is greater than the amplitude of the first peak. The waveform is generated by switching capacitance configuration in the defibrillator from a parallel configuration to a series configuration while the defibrillator is delivering the defibrillation shock to the patient. Because of the switching capacitances and/or the waveform, the external defibrillator can be made physically smaller and weigh less, without sacrificing the therapeutic effect of a larger external defibrillator that would deliver a defibrillation shock of higher energy. As such, the defibrillator is easier to configure for transporting, handling, and even wearing.

35 Claims, 9 Drawing Sheets

*DEFIBRILLATION SCENE*

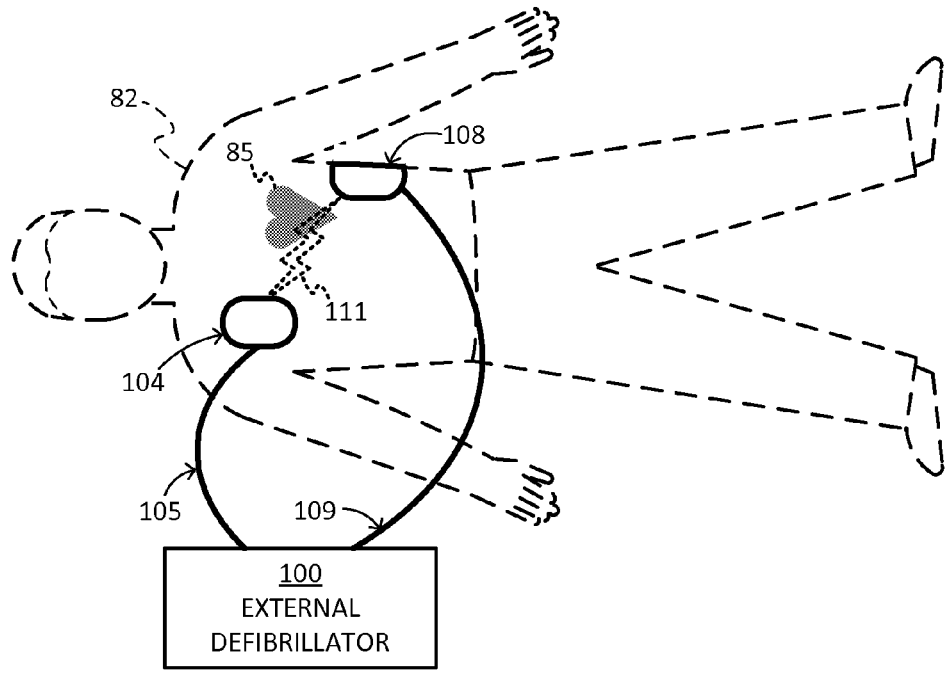
FIG. 1  *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  *EXAMPLES OF EXTERNAL DEFIBRILLATORS*

COMPONENTS OF EXTERNAL DEFIBRILLATOR

*EXTERNAL DEFIBRILLATION WITH SEQUENTIAL STACKED CAPACITOR WAVEFORM*

*ALTERNATIVE EXTERNAL DEFIBRILLATION WITH SEQUENTIAL STACKED CAPACITOR WAVEFORM*

*ALTERNATIVE EXTERNAL DEFIBRILLATION WITH SEQUENTIAL STACKED CAPACITOR WAVEFORM*

*SEQUENTIAL STACKED TWO-CAPACITOR CIRCUITS*

*SEQUENTIAL STACKED THREE-CAPACITOR CIRCUITS*

FIG. 11   *METHODS*

METHODS

SEQUENTIAL STACKED CAPACITOR DEFIBRILLATOR AND WAVEFORM GENERATED THEREFROM

RELATED APPLICATION

This application is related to and claims the benefit of priority of U.S. Provisional Patent Application Ser. No. 61/682,156, filed on Aug. 10, 2012, the disclosure of which is incorporated by reference herein.

BACKGROUND

In humans, the heart beats to sustain life. In normal operation, the heart pumps blood through the various parts of the body. In particular, the various chambers of the heart contract and expand periodically, and coordinated so as to pump the blood regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle then expels the blood, forcing it to circulate to the various parts of the body.

The heart chambers pump because of the heart's electrical control system. In particular, the sinoatrial (SA) node generates an electrical impulse, which generates further electrical signals. These further signals cause the above-described contractions of the various chambers in the heart to take place in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a lifesaving device called a defibrillator. A defibrillator, if applied properly, can administer an electrical shock to the heart. The shock may terminate the VF, thus giving the heart the opportunity to resume pumping blood. If VF is not terminated, the shock may be repeated, sometimes at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. To-date, for some people who are considered to be at a higher risk of VF or other heart arrythmias, an Implantable Cardioverter Defibrillator (ICD) is implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at a high risk. Cardiac events can be experienced by people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them. The time from the collapse to the time a portable defibrillator is applied to the cardiac event victim is critical. Often, a physician can perceive and determine that a patient is at a risk that would qualify the patient for the invasive ICD implant. In such cases, a wearable defibrillator/monitoring device would be highly desirable.

During VF, the person's condition deteriorates, because the blood is not flowing to the brain, heart, lungs, and other organs, which can be damaged as a result. Accordingly, defibrillation must be applied quickly, to restore the blood flow. To expedite defibrillation, there have been efforts to make defibrillators ubiquitous, portable and, when needed, wearable by a prospective patient. All these efforts can be facilitated by making an external defibrillator smaller and weigh less. A persisting need exists for a smaller, lighter, and more portable defibrillator without compromising therapy and/or monitoring efficacy.

BRIEF SUMMARY

In one embodiment, an external defibrillator delivers electrical therapy to a patient using a waveform that includes two or more peaks, which can be adapted by the external defibrillator for different patient impedances (e.g., up to 200 ohms). The second peak has greater amplitude than the first peak.

The defibrillator, in one embodiment, includes a discharge circuit configured to deliver energy to the patient. The defibrillator also includes an energy storage module that is coupled to the discharge circuit. The energy storage module includes two or more energy storage capacitors that are configured to be coupled together in a first manner having a first capacitance, discharge in the first manner to the patient via the discharge circuit, and during discharge in the first manner switch to being coupled together in a second manner. The second manner has a second capacitance that is different from the first capacitance. The resulting waveform is a defibrillation shock that is characterized by a set of at least two peaks. The amplitude of the second peak is greater than the amplitude of the first peak.

Because of the defibrillation waveform, the defibrillation shock can be as effective as a conventional defibrillation shock of a higher energy. Accordingly, an external defibrillator can be made according to embodiments of the invention physically smaller and weigh less, without sacrificing the therapeutic effect of a larger external defibrillator that would deliver a higher energy defibrillation shock. As such, a defibrillator made according to embodiments of the invention is easier to configure for transporting, handling, and, when desirable, wearing.

These and other features and advantages of this description will become more readily apparent from the following Detailed Description, which proceeds with reference to the drawings.

BRIEF DESCRIPTION OF THE DRAWINGS

FIG. 1 is a diagram of a scene where an external defibrillator is used to save the life of a person according to embodiments.

FIG. 2 is a table listing examples of types of the external defibrillator shown in FIG. 1, and who they might be used by.

DETAILED DESCRIPTION

Figure 3:
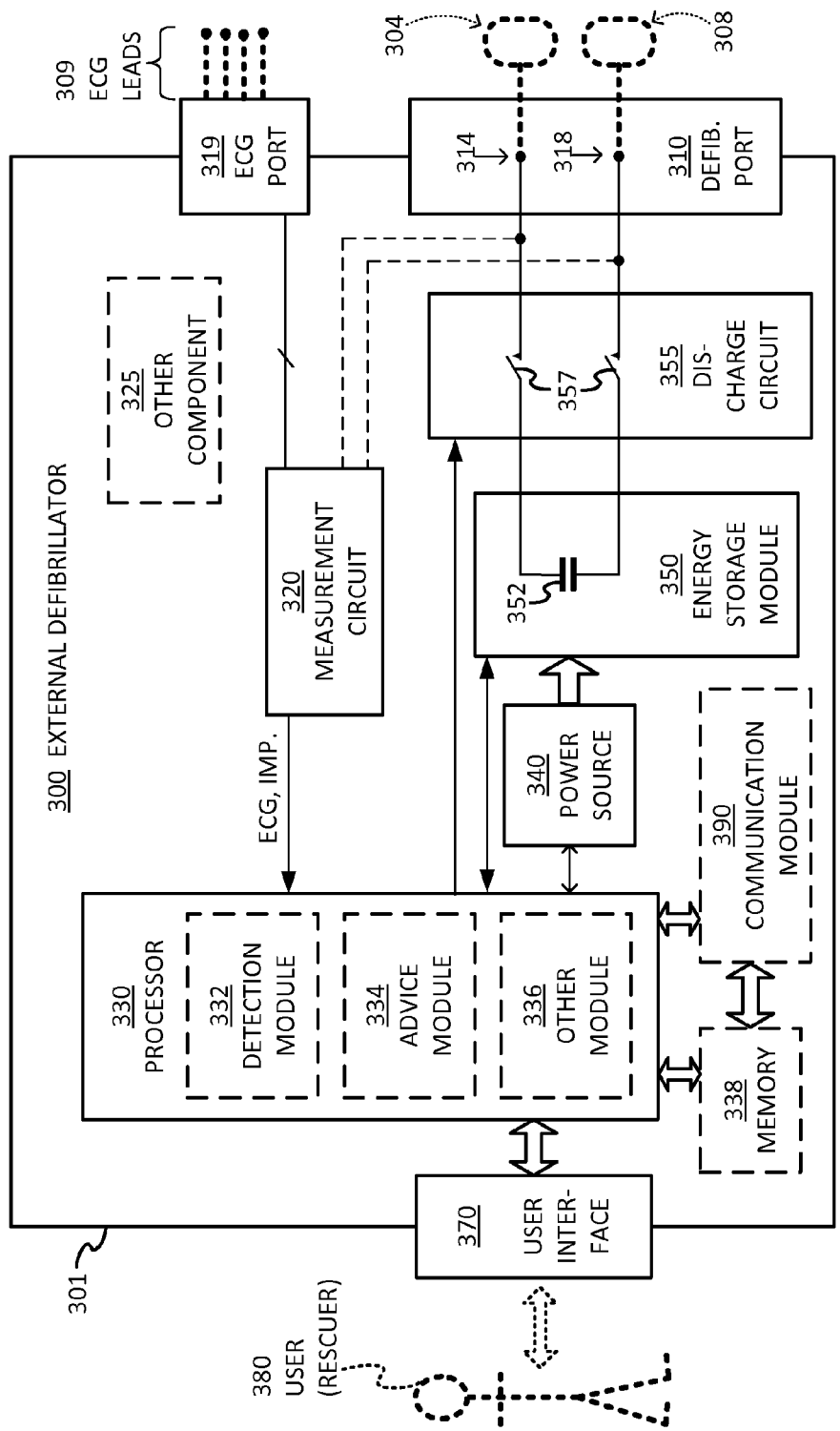
FIG. 3 is a diagram showing components of an external defibrillator, such as the one shown in FIG. 1, which is made according to embodiments.

As has been mentioned, the present description is about external defibrillators, processors, and methods of delivering electrical therapy using a waveform that can be generated by an external defibrillator that uses a sequential stacked capacitor. In one or more implementations, the waveform includes two or more peaks in a phase. The second peak has greater amplitude than the first peak. Embodiments are now described in more detail.

Defibrillation Scene

FIG. 1 is a diagram of a defibrillation scene. A portable external defibrillator 100 is being applied to a person 82. Person 82 could be experiencing a condition in their heart 85, which could be Ventricular Fibrillation (VF) or a different arrhythmia. The scene of FIG. 1 could be in a hospital, where person 82 is a patient, or in some other location where an SCA victim is unconscious and then turned to be on their back. Alternatively, person 82 could be someone who is wearing defibrillator 100.

Defibrillator 100 is usually provided with at least two defibrillation electrodes 104, 108, which are sometimes called just electrodes 104, 108. Electrodes 104, 108 are coupled with external defibrillator 100 via respective electrode leads 105, 109. A rescuer (not shown) has attached electrodes 104, 108 to the skin of person 82. Alternatively, if defibrillator 100 is wearable, electrodes 104, 108 have been applied to the skin before the event, or automatically.

Defibrillator 100 is configured to administer electrical therapy 111 to person 82. In other words, defibrillator 100 can cause, via electrodes 104, 108, electrical energy to go through the body of person 82, in an attempt to affect heart 85. Therapy 111 can include a brief, strong defibrillation pulse, which is also known as a defibrillation shock, in an attempt to restart heart 85 so as to save the life of person 82.

Defibrillator 100 can be one of different types, each with different sets of features and capabilities. The set of capabilities of defibrillator 100 is determined by planning who would use it, and what training they would be likely to have. Examples are now described.

Types of External Defibrillators

FIG. 2 is a table listing examples of types of external defibrillators, and who they are primarily intended to be used by. One of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is typically intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering of the shock.

As a patient monitor, the device has features additional to what is minimally needed for mere operation as a defibrillator. These features can be for monitoring physiological indicators and other data of a person in an emergency scenario. These physiological indicators and other data are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

Another type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a simpler construction, an AED typically costs much less than a defibrillator-monitor. As such, it makes sense for a hospital, for example, to, as a back-up, deploy AEDs at its various floors, in case the more expensive defibrillator-monitor is more critically being deployed at an Intensive Care Unit, and so on.

AEDs can also be used by people who are not in the medical professions. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

With either of the described-above types of defibrillator, a cardiac victim must depend on prompt responsiveness of a bystander/rescuer. Another type of such a defibrillator is a wearable defibrillator, which is configured so that it can be worn by the patient for long time durations. These time durations are preferably days and weeks, and in any event at least one hour. Wearable defibrillator is capable of automatic autonomous response to a cardiac event. The delay from the onset of the event to the administration of therapy/care is in this case dramatically reduced. There are additional types of external defibrillators, which are not listed in FIG. 2. For example, a hybrid defibrillator can have aspects of an AED, and also of a defibrillator-monitor. A usual such aspect is additional ECG monitoring capability. Other types of defibrillators are possible, as would be apparent to a person skilled in the art.

Example External Defibrillator

FIG. 3 is a diagram showing components of an example external defibrillator 300 made according to embodiments, in which a novel discharge circuit and waveform are provided. These components can be, for example, in external defibrillator 100 of FIG. 1. Plus, these components of FIG. 3 can be provided in a housing 301, which is also known as casing 301 or may work as a system 301 comprised of modular components interacting with one another.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, defibrillator 300 could have additional ports (not shown), and another component 325 for the above described additional features, such as patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 is an article that may be implemented in any number of ways. Such ways include, by way of example and not of limitation, digital and/or analog processors such as microprocessors and digital-signal processors (DSPs); controllers such as microcontrollers; software running in a machine or a chip; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated by or included in processor 330, in whole or in part, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, acquired or entered data about patient 82, etc.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy can be stored, when it is being prepared for sudden discharge to administer one or more electrical discharges, as will be described later in this document. Module 350 can be charged from power source 340 to the right amount of energy, as controlled by processor 330. In typical implementations, module 350 includes two or more capacitors 352, and so on. Energy storage module 350 typically becomes recharged, after it delivers energy. Opportune times for such recharging are after delivering the defibrillation shock 448 described below. More aggressive recharging may be needed depending factors such as the patient's bulk impedance.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. The circuit 355 can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer about their resuscitation attempts, and so on. Interface 370 may also be able to issue audible prompts, such as by having a speaker for voice prompts, etc. Interface 370 may additionally include various controls, such as pushbuttons, keyboards, touchscreens, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

As mentioned above, defibrillator 300 is capable of delivering therapy using a waveform. More particularly, processor 330 may determine whether defibrillation is advised for the patient, for example by using advice module 334. If defibrillation is indeed advised, processor 330 may control delivery of the energy stored in energy storage module 350. The therapy is in the form of a special waveform, as is now described in more detail.

Example Timing Diagrams

Figure 4:
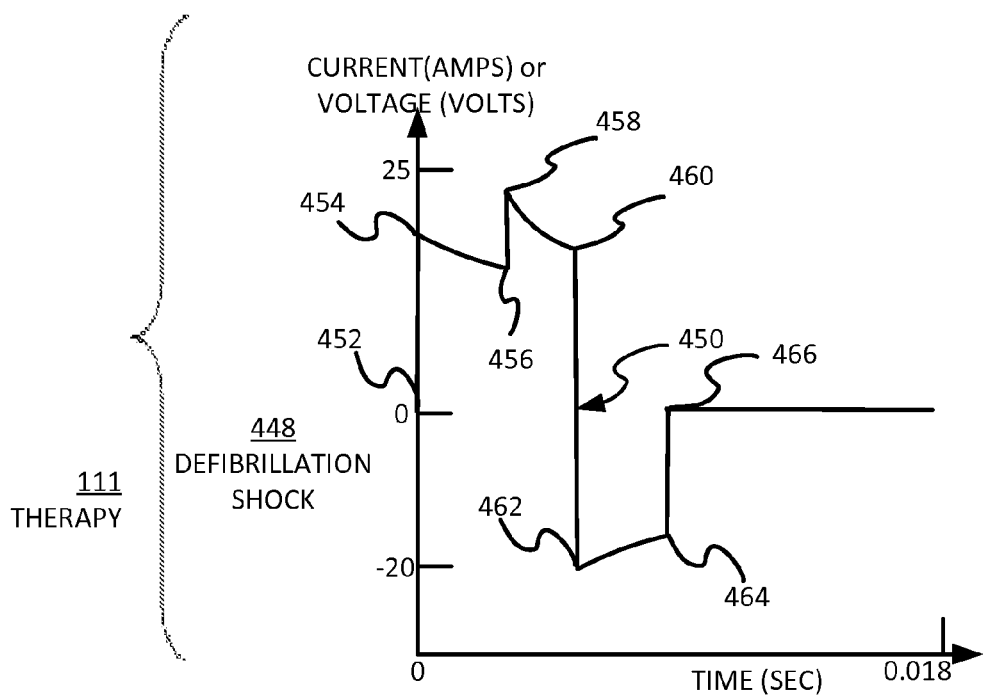
FIG. 4 is a timing diagram for illustrating the timing of a waveform according to embodiments.

FIG. 4 is a timing diagram for illustrating the timing of a waveform according to embodiments. Therapy 111 is shown along a time axis and a current axis, in terms of icons that represent delivery of energy to the patient as therapy. It will be understood that, in some embodiments, the energy of therapy 111 is delivered automatically, in response to determining that defibrillation is advised for the patient. In other embodiments, the energy is delivered responsive to a user operating the user interface 370; in those embodiments, the user would be informed that defibrillation is advised, or to activate a control, or both. In some embodiments, the energy delivered as therapy is delivered as a defibrillation shock in a waveform, as described in more detail below. It will also be understood that the current axis can also schematically represent the voltage of therapy 111, as indicated in FIG. 4. For clarity, in the descriptions below, waveforms will be described in terms of current, but it should be understood that the waveforms could be described equally well in terms of voltage.

Therapy 111 includes energy delivered as a defibrillation shock 448. Defibrillation shock 448 can be delivered in any way known in the art. For example, shock 448 illustrated in FIG. 4 is a biphasic shock (in this context biphasic refers to a positive phase a negative phase, each such phase having at least 1 peak). However, the defibrillation shock could be a monophasic shock or other multiphasic shock. Shock 448 could be delivered by only two electrodes, or it could be a multi-vector shock, such as from multiple electrodes or segmented electrodes with different active segments.

For external shocks for an adult VF defibrillation shock 448 has energy of at least 120 Joules (J). Subsequent shocks may escalate higher, up to 360 J, for example. For conditions other than VF, such as atrial fibrillation (AF) a smaller initial shock may be used (e.g. 50 J).

The defibrillation energy can be smaller, if the patient is a child or an infant. For example, for external shocks for adult VF, generally shocks of 120 J or more are used for the initial shock. Subsequent shocks may escalate higher, possibly up to 360 J. For other conditions, such as atrial fibrillation (AF) a smaller initial shock may be used, possibly as low as 50 J.

Therapy 111 includes energy delivered as a waveform 450 of varying rising and falling current levels over time as the defibrillation shock 448. For example, at time t=0 the amplitude of the waveform 450 rapidly rises from zero amps at point 452 to a first peak 454. The waveform 450 then decays exponentially to a point 456. The waveform 450 rapidly rises to a second peak 458 and then decays exponentially to a point 460. As can be seen in FIG. 4, these two peaks occur in a positive first portion of waveform 450 in this example. The amplitude of the waveform 450 then drops rapidly to a point 462 and increases exponentially to a point 464. The waveform 450 then rises rapidly to a point 466. As can be seen in FIG. 4, a negative peak occurs in a negative second portion of waveform 450 in this example.

In some embodiments, processor 330 is configured to determine whether defibrillation is advised for the patient by performing an analysis of an ECG of the patient. For example, the ECG may indicate that the patient has VF or Ventricular Tachycardia ("VT"). In some of these embodiments, the energy of therapy 111 is ultimately delivered via electrodes, and the ECG is received from the patient via the same electrodes. An example is now described.

The above embodiments are not limiting for practicing embodiments of the invention. For example, the defibrillation shock 448 can have a different waveform.

Further, while only two peaks 454 and 458 are shown for the positive portion, embodiments of the invention could be practiced with more. For example, there could be three or more peaks in the positive portion of the waveform 450. Moreover, the polarities of the waveform 450 can be reversed such that at time t=0 the amplitude of the waveform can rapidly fall from zero amps to a first negative peak, increase exponentially to a point where the waveform rapidly falls to a second negative peak that is greater in amplitude than the first peak in a negative first portion of the waveform. The waveform could then increase exponentially and then rise rapidly in a positive second portion of the waveform to a point where the waveform decreases exponentially. The waveform amplitude then rapidly falls.

In addition, all of what is written in this document about treating VF can also be used for treating other cardiac arrhythmias, such as shockable Ventricular Tachycardia ("VT"). Such could be performed with a synchronized cardio-version shock that includes the waveform 450.

In some embodiments, measurement circuit 320 measures an impedance of the patient, while defibrillation shock 448 is being delivered. In such embodiments, capacitor 352 can be charged for delivering the waveform 450 to a value determined from the measured impedance.

In some embodiments, the measurement circuit 320 measures the patient's impedance before a discharge (or perhaps after), but not during. To do this, the measurement circuit 320 applies a low-level current (e.g., 100 uA) at a relatively high frequency (e.g., 20 kHz) to determine the impedance. This value can be used to determine the charge voltage. In other embodiments, the patient impedance may be measured by making high voltage measurements during the discharge.

In some embodiments the patient impedance may be measured during the delivery of the high voltage shock waveform. In various embodiments, this measurement may be in addition to or instead of the impedance measurement used to charge capacitor 352. A high voltage measurement may be considered advantageous because it may provide a more accurate indication of the actual impedance to a defibrillation shock than a low level measurement. A high voltage measurement of the patient impedance is sometimes referred to as a "dynamic" patient impedance because it is made during the shock and allows shock parameters to be adjusted on the fly.

There are various methods of measuring a dynamic patient impedance. One method is to measure the voltage and current applied to the patient and take the ratio according to Ohm's law. The voltage may be measured directly across the patient, or across the capacitor bank, depending on needs of the application. The current can be measured with a current measuring circuit. One method of implementing a current measuring circuit is to include a low value resistor (e.g. 0.1 ohms) in series with the patient. This impedance has little effect on the shock waveform. The voltage can be measured across the resistance to determine the patient current.

Another method of measuring a dynamic patient impedance is to monitor the change in capacitor voltage over time. This method has the advantage of not requiring a current measuring circuit. The patient impedance can be measured using this method using the formula $$\frac{Vfinal}{Vinitial} = e^{\frac{-t}{R*C}},$$

where Vinitial is a first voltage measurement, Vfinal is a second voltage measurement, t is the time between the measurements, C is the value of the energy storage capacitor, and R is the patient impedance. Vinitial and Vfinal can be made at any two points during the shock waveform.

Figure 5:
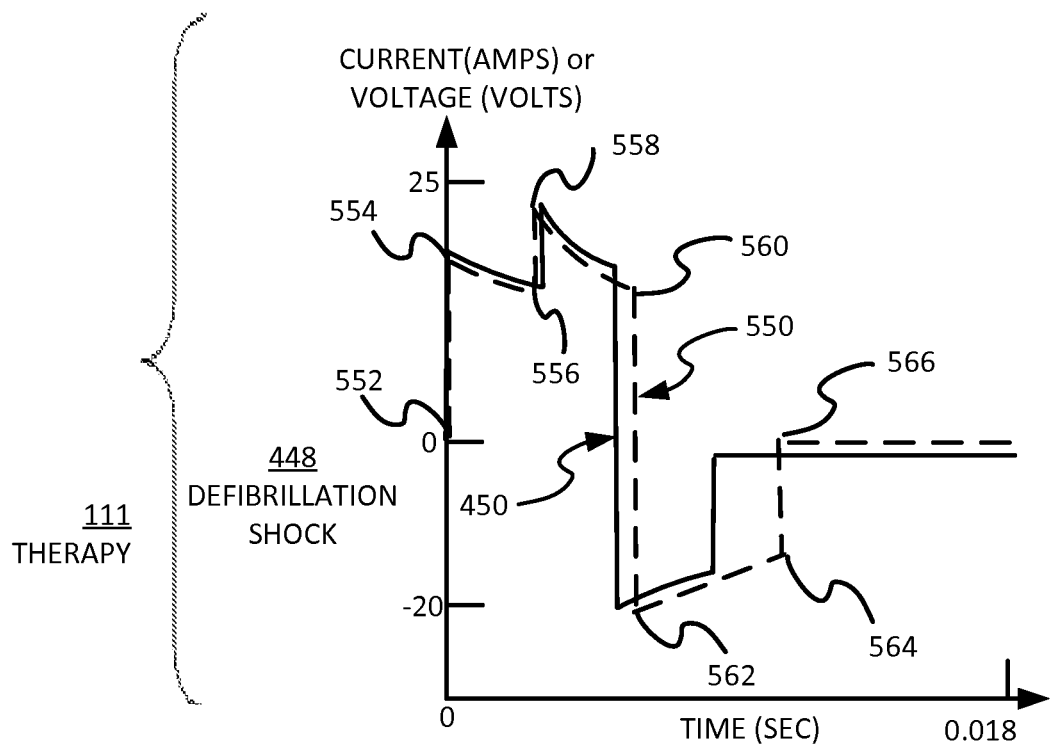
FIG. 5 is a timing diagram for illustrating the timing of a waveform according to alternative embodiments.

FIG. 5 is a timing diagram for illustrating the timing of a waveform alternative according to embodiments. In the illustrated embodiment, therapy 111 includes energy delivered as waveform 450 and a waveform 550, each having varying rising and falling current levels over time. The durations of the various risings and fallings (referred to as "phases" herein) may be determined based on a measurement of a patient-related parameter, such as a patient's impedance. For example, at time t=0 the amplitude of the waveform 550 rapidly rises from zero amps at point 552 to a first peak 554. The waveform 550 then decays exponentially to a point 556. The waveform 550 rapidly rises to a second peak 558 and then decays exponentially to a point 560. The amplitude of the waveform 550 drops rapidly to a point 562 and increases exponentially to a point 564. The waveform 550 then rises rapidly to a point 566. Point 566 is at zero amps, but is shown slightly offset in FIG. 4 to be visible along with waveform 450. As mentioned, in some embodiments, the duration of the phases can be determined based on the patient's impedance. For example, in one embodiment, external defibrillator 300 (FIG. 3) determines the patient's impedance via measurement circuit 320 and/or measures the dynamic patient impedance as described above. Based on this impedance, external defibrillator 300 in this embodiment determines the time at which to output more current, represented in waveform 550 as rising from point 556 to point 558. Similarly, external defibrillator 300 in this example embodiment determines the time at which to cause current to flow in the opposite direction, represented in waveform 550 as dropping from point 560 to point 562, and so on for the last phase. Embodiments of external defibrillator 300 are capable of automatically adapting to a relatively large range of patient impedances of up to approximately 200 ohms (compared to a maximum impedance of less than 90 ohms for implantable defibrillators). Embodiments of external defibrillator 300 are configured to automatically adjust the shock waveform individually for each patient.

Figure 6:
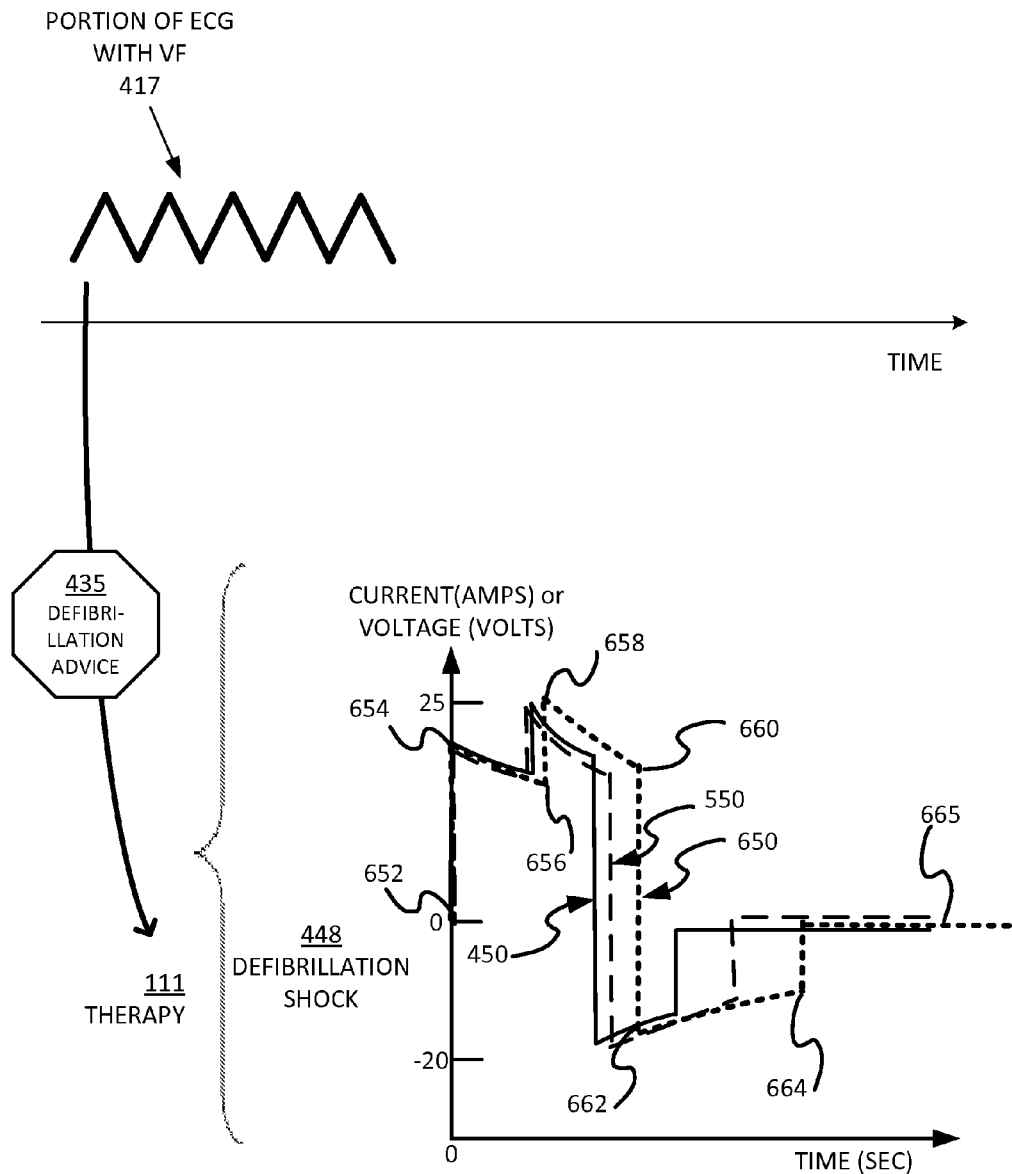
FIG. 6 is a timing diagram for illustrating the timing of a waveform according to alternative embodiments.

FIG. 6 is a timing diagram for illustrating the timing of a waveform alternative according to embodiments. In the illustrated embodiment, therapy 111 includes energy delivered as waveform 450, waveform 550, and a waveform 650, each having varying rising and falling current levels over time. For example, at time t=0 the amplitude of the waveform 650 rapidly rises from zero amps at point 652 to a first peak 650. The waveform 650 then decays exponentially to a point 656. The waveform 650 rapidly rises to a second peak 658 and then decays exponentially to a point 660. The amplitude of the waveform 650 drops rapidly to a point 662 and increases exponentially to a point 664. The waveform 650 then rises rapidly to a point 665.

In one embodiment the duration of every phase of the waveform may be determined completely or in part according to a single measurement of a patient related parameter. For example, a parameter such as the patient impedance could be measured before the start of the shock using circuit 320 and each phase of the shock would be calculated based on that measurement. Alternatively, the impedance could be dynamically measured between points 654 and 656 and the duration of all phases of the shock based on those measurements.

However, it is possible that the impedance of the patient may change during the shock, in which case basing the phase durations on a single measurement would be sub-optimal. This would be particularly likely if current peak 658 was significantly higher than peak 654. The shock impedance tends to drop at higher currents, so a single measure may not accurately reflect the impedance for the entire shock.

Another embodiment would make multiple measurements of the patient-related parameter during the shock. For example, one dynamic impedance measurement could be made between points 654 and 656. Those measurements would be used to adjust the duration of that phase. A second measurement could be made between points 658 and 660. Those measurements would be used to adjust the duration of that phase. The negative phase of the shock could be adjusted based on one or both of the previous measurements, or on an independent measurement during that phase.

Although the same formula can be used for calculating the impedance of each phase, it should be noted that the capacitance of each phase may be different, so the value of "C" in the formula $$\frac{Vfinal}{Vinitial} = e^{\frac{-t}{R*C}}$$

may be different for each phase.

EXAMPLE CIRCUITS

Figure 7:
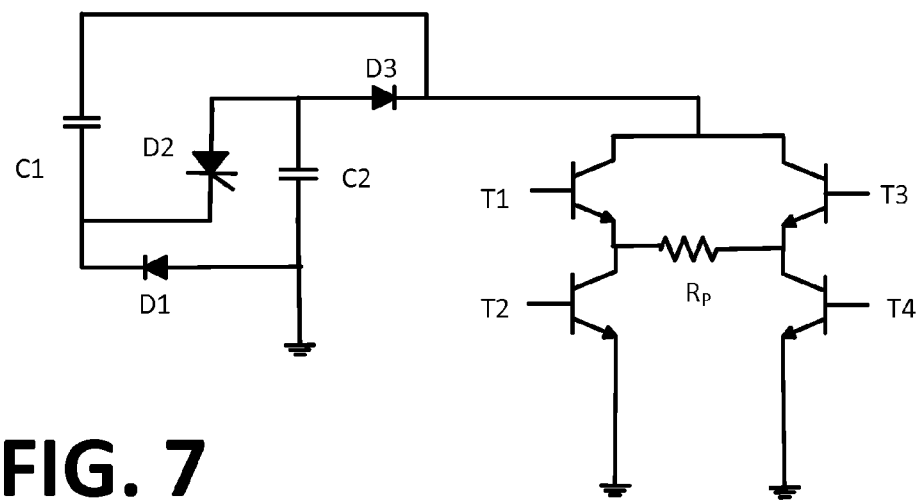
FIGS. 7 through 10 are circuits for implementing a waveform according to embodiments.

FIG. 7 is a circuit for implementing a waveform according to embodiments. In the embodiment illustrated in FIG. 7, the circuit includes two energy storage capacitors C1 and C2, diode D1, silicon-controller rectifier (SCR) D2, diode D3, and transistors T1, T2, T3, and T4. FIG. 7 also shows a resistance $R_P$, which represents resistance that a patient presents to the external defibrillator 300.

The circuit illustrated in FIG. 7 can be implemented in the energy storage module 350 and the discharge circuit 355. For example, the capacitors C1 and C2 represent the capacitor 352 in the external defibrillator 300. The transistors T1, T2, T3, and T4 represent the switch 357 in the external defibrillator 300.

In the embodiment illustrated in FIG. 7, the capacitor C1 has a first terminal coupled to a first terminal of the diode D3, and to the collectors of transistors T1 and T3. The capacitor C1 has a second terminal coupled to a first terminal of the diode D1 and to a first terminal of the SCR D2. The SCR D2 has a second terminal coupled to a first terminal of capacitor C2 and to a second terminal of diode D3. A second terminal of diode D1 is coupled to a second terminal of capacitor C2 and ground.

Also in the embodiment illustrated in FIG. 7, the emitter of transistor T1 is coupled to the collector of transistor T2, and the emitter of the transistor T3 is coupled to the collector of transistor T4. The emitters of transistors T2 and T4 are coupled to ground. The resistance $R_P$ is coupled to the emitters of transistors T1 and T3 and the collectors of transistors T2 and T4.

The circuit illustrated in FIG. 7 operates as follows. When power is applied, Transistors T1, T2, T3, and T4 are all turned off. SCR D2 is also turned off. Capacitors C1 and C2 are charged from a power source 340 (shown in FIG. 3). Capacitors C1 and C2 in one embodiment may have example values of approximately 120 uF each, and in other embodiments may range from 50 uF to 500 uF. After charging, the total energy stored in C1 and C2 may typically be approximately 150 J, but could range from 50 J to 360 J. In order to store an example value of 150 J, two 120 uF capacitors would have a voltage rating of approximately 1120V.

Current flow to the patient begins when two of the transistors, such as T1 and T4, are turned on. Capacitors C1 and C2 discharge in parallel into the patient.

After a period of time Time1, SCR D2 is turned on, causing capacitors C1 and C2 to be switched to a series configuration. SCR D2 is turned on while current is flowing to the patient, and current flow to the patient continues with the capacitors C1 and C2 in series.

The period of time Time1 may be determined by processor 330 according to a patient-related parameter. The patient-related parameter may be measured during the defibrillation shock or prior to the start of the shock. The patient-related parameter may be the patient's impedance, but it could also be another physiological signal, such as an measurement of the ECG signal, or it could be an electrical measurement such as the rate of discharge of one or more of the capacitors C1 and/or C2. Other patient-related parameters include a measurement of a current level, a capacitor voltage, a patient voltage, a rate of decay of a capacitor voltage, a rate of decay of a patient voltage, an energy delivered, or a charge delivered to the patient. The time Time1 may typically be about 4 mS, but could vary from 0.1 mS to 10 mS.

After a period of time Time2, transistors T1 and T4 are turned off and transistors T2 and T3 are turned on. This causes the polarity of the current flow to the patient to be reversed, causing the patient to receive a biphasic shock waveform. SCR D2 remains turned on, and capacitors C1 and C2 continue to be discharged in series. The value of time Time2 may be determined based on Time1, or it may be determined based on a patient-related parameter. The patient-related parameter used to determine Time2 may be the same as the patient-related parameter used to determine Time1, or it may be different. Time2 may typically be 60 mS from the start of the shock, but it may vary from 5 mS to 20 mS.

After a period of time Time3, transistors T2 and T3 are turned off. This terminates current flow to the patient. SCR D2 turns off by itself when current flow stops.

Transistors T1, T2, T3, and T4 in FIG. 7 form a circuit configuration known as an "H-bridge." Those skilled in the art will realize that while transistors T1, T2, T3, and T4 are represented as bipolar transistors, they could be replaced other switching components. For example, Insulated Gate Bipolar Transistors (IGBTs), Metal Oxide Semiconductor Field Effect Transistors (MOSFETs), Bipolar Metal Oxide Semiconductor Field Effect Transistors (BiMOSFETs) or other high-voltage switching components could all work in this application. Similarly, D2 is shown here as an SCR, but other types of high-voltage switches could also serve the function D2 serves.

In order to deliver a stepped waveform to the patient, transistors T1, T2, T3, and T4 are be capable of handling sufficient voltage and current to deliver at least an exemplary approximately 150 J, for example, without failing. If the capacitors C1 and C2 have a voltage of approximately 1120V to store 150 J, then some of the transistors T1, T2, T3, and T4 have a voltage standoff capability of up to double the capacitor voltage, or 2240V. The capacitors C1 and C2 have partly discharged when they are switched into the series configuration so the actual peak voltage that the transistors T1, T2, T3, and T4 withstand may be somewhat less than double the capacitor voltage.

The circuit of FIG. 7 is advantageous, in part, because it only uses a single active semiconductor (SCR D2) to switch the capacitors from a parallel configuration to a series configuration.

This switching of the capacitors C1 and C2 from parallel to series-coupled also generates a waveform. In one implementation, at time t=0, the waveform rises to a first amplitude. At time t>0, the waveform decays exponentially to a second amplitude, rises to a third amplitude higher than the first and the second amplitude, and then decays exponentially to a fourth amplitude. The also waveform may fall to a fifth amplitude less than the first, second, and third amplitudes.

For example, when the capacitors C1 and C2 are in a parallel configuration the waveform rises to a first peak (454 of FIG. 4). The capacitors C1 and C2 then discharge exponentially to a point (456 of FIG. 4). When the capacitors C1 and C2 are switched to a series configuration the waveform rapidly rises to a second peak (458 of FIG. 4) and the capacitors C1 and C2 discharge exponentially to a point (460 of FIG. 4).

Alternatively, the polarity of the waveform may be reversed and the switching generates a waveform that, at time t=0, falls to a first amplitude. At time t>0, the waveform increases exponentially to a second amplitude, falls to a third amplitude greater than the first and the second amplitude, and then increases exponentially to a fourth amplitude.

Figure 8:
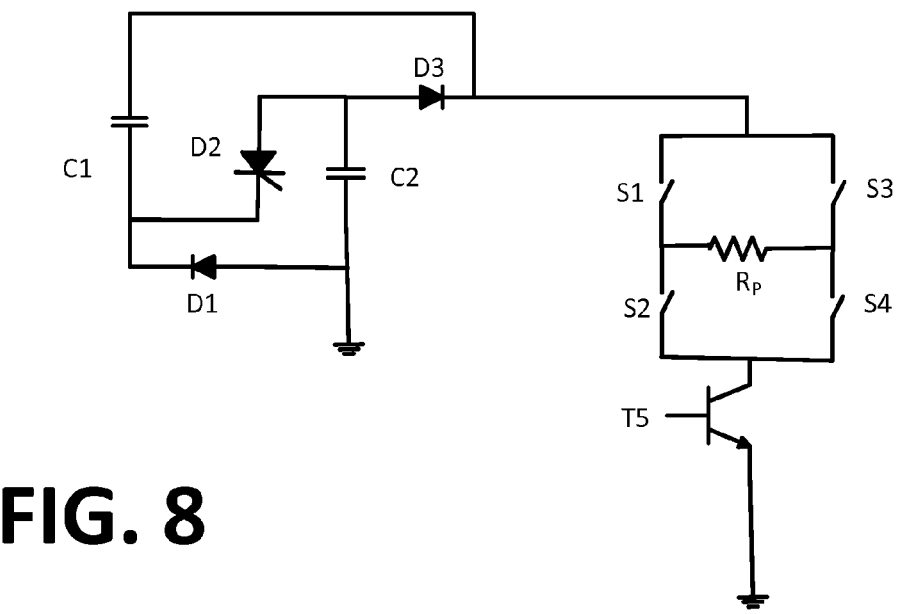

FIG. 8 is a circuit for implementing a waveform according to alternative embodiments. The embodiment illustrated in FIG. 8 is similar to the embodiment illustrated in FIG. 7. For example, the circuit includes energy storage capacitors C1 and C2, diode D1, SCR D2, diode D3, and patient resistance $R_P$. However, transistors T1, T2, T3, and T4 are replaced with switches S1, S2, S3, and S4, and they are coupled to the emitter of a transistor T5. For example, in some embodiments switches S1, S2, S3 and S4 can be implemented with relays or mechanical switches.

The circuit in FIG. 8 operates in a manner that is similar to the circuit in FIG. 7. When power is applied, switches S1, S2, S3, and S4 are all open. SCR D2 and transistor T5 are turned off. Capacitors C1 and C2 are charged from a power source 340 (shown in FIG. 3). Current flow to the patient begins when two of the switches, such as S1 and S4, are closed and transistor T5 is turned on. Capacitors C1 and C2 discharge in parallel into the patient.

After a period of time Time1, SCR D2 is turned on, causing capacitors C1 and C2 to be switched to a series configuration. SCR D2 is turned on while current is flowing to the patient, and current flow to the patient continues with the capacitors C1 and C2 in series.

After a period of time Time2, transistor T5 is turned off and switches S1 and S4 are opened. Switches S2 and 3 are then closed and transistor T5 is turned back on. This causes the polarity of the current flow to the patient to be reversed, causing the patient to receive a biphasic shock waveform. SCR D2 remains turned on, and capacitors C1 and C2 continue to be discharged in series.

After a period of time Time3, transistor T5 is turned off. This terminates current flow to the patient. SCR D2 turns off by itself when current flow stops. Switches S2 and S3 are then opened.

This switching of the capacitors C1 and C2 from parallel to series-coupled also generates a waveform. The waveform is characterized by a set of at least two peaks. The second peak has greater amplitude than the first peak.

For example, at time t=0, the waveform rises to a first amplitude. At time t>0, the waveform decays exponentially to a second amplitude, rises to a third amplitude higher than the first and the second amplitude, and then decays exponentially to a fourth amplitude. The also waveform may fall to a fifth amplitude less than the first, second, and third amplitudes.

Alternatively, the polarity of the waveform may be reversed and the switching generates a waveform that, at time t=0, falls to a first amplitude. At time t>0, the waveform increases exponentially to a second amplitude, falls to a third amplitude greater than the first and the second amplitude, and then increases exponentially to a fourth amplitude.

Figure 9:
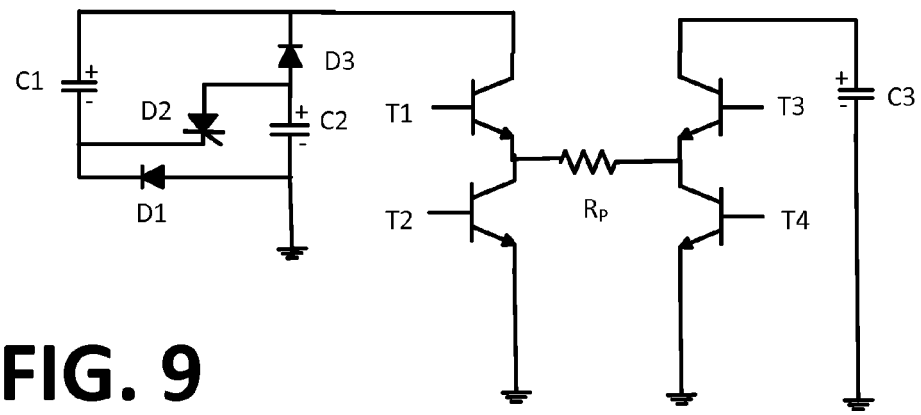

FIG. 9 is a circuit for implementing a waveform according to embodiments. In the embodiment illustrated in FIG. 9, the circuit includes three energy storage capacitors C1, C2, and C3, diode D1, SCR D2, diode D3, and transistors T1, T2, T3, and T4. The circuit also includes the resistance $R_P$, which represents resistance that a patient presents to the external defibrillator 300.

The circuit illustrated in FIG. 9 can be implemented in the energy storage module 350 and the discharge circuit 355. For example, the capacitors C1, C2, and C3 represent the capacitor 352 in the external defibrillator 300. The transistors T1, T2, T3, and T4 represent the switch 357 in the external defibrillator 300.

In the embodiment illustrated in FIG. 9, the capacitor C1 has a first terminal coupled to a first terminal of the diode D1. The capacitor C1 has a second terminal coupled to a first terminal of diode D3 and the collector of the transistor T1. A second terminal of diode D3 is coupled to a first terminal of SCR D2 and a first terminal of capacitor C2. A second terminal of diode D1 is coupled to a second terminal of capacitor C2 and ground. The capacitor C1 also has its first terminal coupled to a second terminal of the SCR D2.

Also in the embodiment illustrated in FIG. 9, the emitters of the transistors T1 and T3 are respectively coupled to the respective collectors of transistors T2 and T4 as well as to a first terminal of resistance $R_P$. The emitters of transistors T2 and T4 are coupled to ground. A second terminal of resistance $R_P$ is coupled to the collectors of transistors T2 and T4. The collector of transistor T is coupled to a first terminal of capacitor C3. A second terminal of capacitor C3 is coupled to ground.

The circuit illustrated in FIG. 9 operates similar to the circuit in FIG. 7 except that the circuit illustrated in FIG. 9 uses three capacitors instead of two. Capacitors C1 and C2 provide the energy for the positive phase of the waveform while capacitor C3 provides the energy for the negative phase. As with FIG. 7, positive current flow is initiated when transistors T1 and T4 are turned on. The capacitors C1 and C2 are switched from a parallel to a series configuration when SCR D2 is closed. Positive current flow stops when transistors T1 and T4 are opened.

Unlike the circuit in FIG. 7, the energy for the negative phase is provided from capacitor C3 instead of capacitors C1 and C2. Current flow begins in the negative direction relative to the patient resistance $R_P$ when transistors T2 and T3 are turned on. Negative current flow through the patient ends when transistors T2 and T3 are turned off.

This switching of the capacitors C1 and C2 from parallel to series-coupled also generates a waveform. The waveform is characterized by a set of at least two peaks. The second peak has greater amplitude than the first peak.

Figure 10:
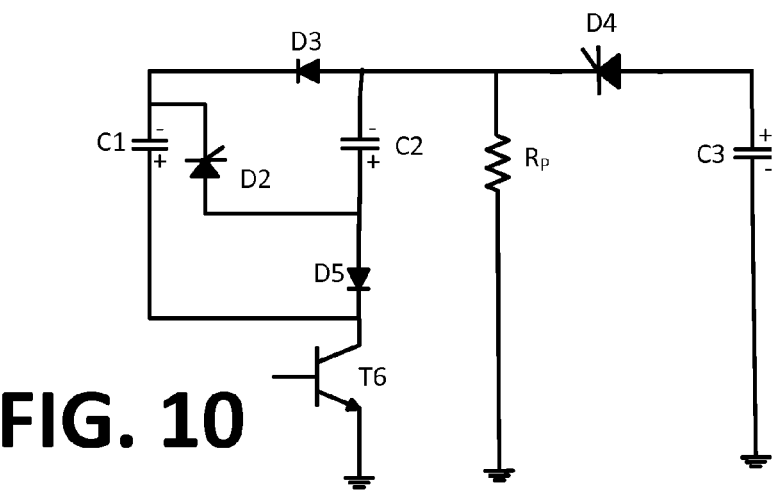

FIG. 10 is a circuit for implementing a waveform according to alternative embodiments. In the embodiment illustrated in FIG. 10, the circuit includes three energy storage capacitors C1, C2, and C3, SCRs D2 and D4, diodes D3 and D5, and transistor T6. The circuit also includes the resistance $R_P$, which represents resistance that a patient presents to the external defibrillator 300.

The circuit illustrated in FIG. 10 can be implemented in the energy storage module 350 and the discharge circuit 355. For example, the capacitors C1, C2, and C3 represent the capacitor 352 in the external defibrillator 300. The transistor T6 and the SCR D4 represent the switch 357 in the external defibrillator 300.

In the embodiment illustrated in FIG. 10, the capacitor C1 has a first terminal coupled to a first terminal of the SCR D2 and a first terminal of diode D3. The capacitor C1 has a second terminal coupled to a first terminal of diode D5 and the collector of transistor T6. Capacitor C2 has a first terminal coupled to a second terminal of SCR D2 and a second terminal of diode D5. Capacitor C2 has second terminal coupled to a second terminal of diode D3, a first terminal of resistance $R_P$, and a first terminal of SCR D4. A second terminal of SCR D4 is coupled to a first terminal of capacitor C3. A second terminal of resistance $R_P$, a second terminal of capacitor C3, and the emitter of transistor T6 are coupled to ground.

The circuit illustrated in FIG. 10 operates as follows. When power is applied transistor T6, and SCRs D2 and D4 are all turned off. Positive current flow begins when transistor T6 is turned on. The capacitors C1 and C2 switch from parallel to series when SCR D2 is activated. Positive current flow stops when transistor T6 is turned off. A negative pulse is given when SCR D4 is turned on. Current flow in the negative phase stops when capacitor C3 is discharged.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to embodiments of the invention. A storage medium according to embodiments of the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to embodiments of the invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods in accordance to embodiments of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

EXAMPLE METHODS

Figure 11:
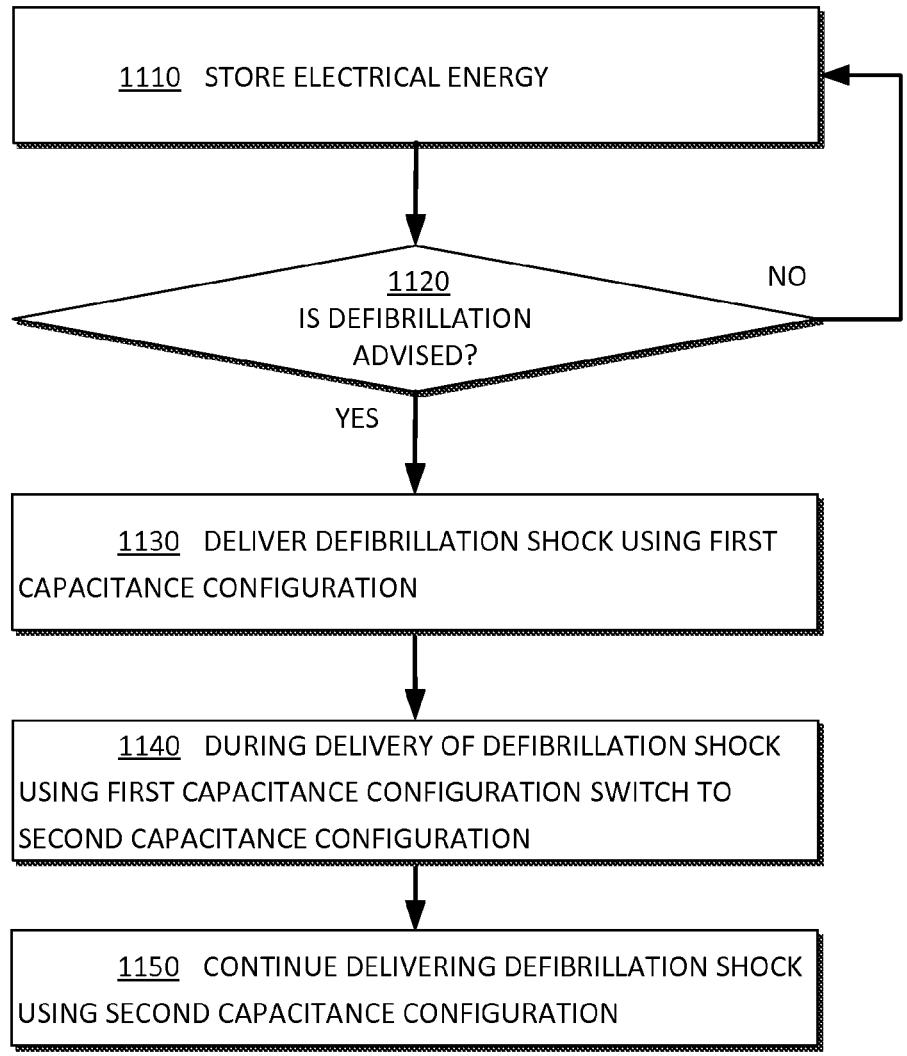
FIG. 11 is a flowchart for illustrating methods according to embodiments.

FIG. 11 shows a flowchart 1100 for describing methods according to embodiments, for an external medical device to deliver electrical therapy to a patient. The method of flowchart 1100 may also be practiced by external defibrillators made according to embodiments described above, such as defibrillator 300.

According to an operation 1110, electrical energy is stored, such as in an energy storage module.

According to a next operation 1120, it is determined whether defibrillation is advised for the patient. Execution branches according to the outcome of operation 1120.

If defibrillation is not advised, execution can return to operation 1110 as shown in the example of FIG. 11, or terminate.

If defibrillation is indeed advised, at operation 1130, a defibrillation shock is delivered to the patient using a first capacitance configuration, such as shown in FIG. 7. As also per the above, the defibrillation shock can be delivered automatically or responsive to a user operating a user interface of the device.

According to a next operation 1140, during delivery of the defibrillation shock at the first capacitance configuration the capacitance configuration switches to a second capacitance configuration, such as shown in FIG. 7. Again as per the above, in some embodiments, the electrical shock at the second capacitance configuration can be delivered without further analyzing an ECG of the patient, and/or without making any other preparation.

According to a next operation 1150, delivery of the electrical shock continues at the second capacitance configuration.

Figure 12:
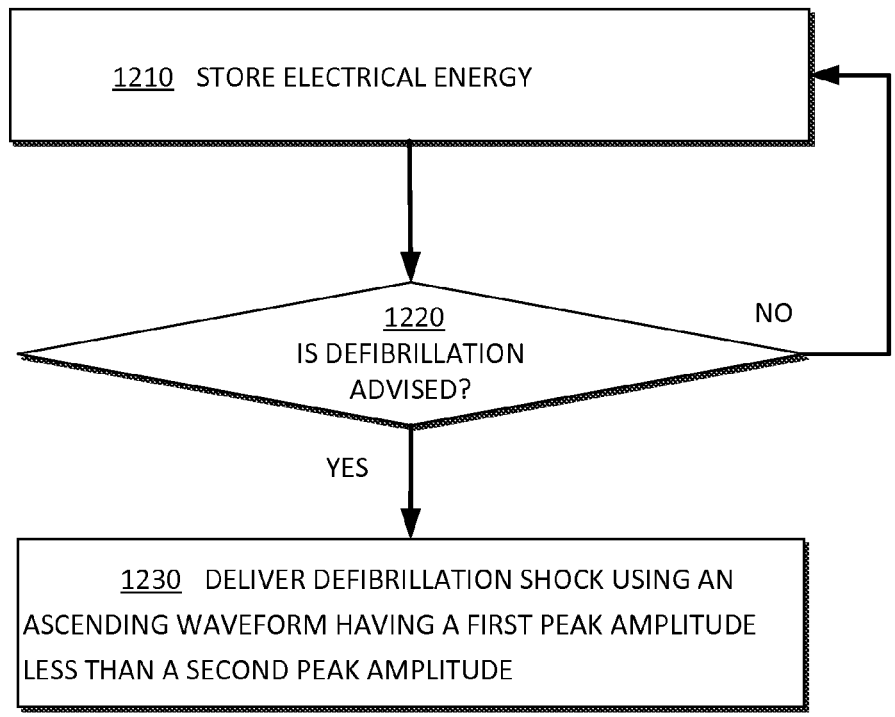
FIG. 12 is a flowchart for illustrating additional methods according to embodiments.

FIG. 12 shows a flowchart 1200 for describing methods according to embodiments for an external medical device to deliver electrical therapy to a patient. The method of flowchart 1200 may also be practiced by external defibrillators made according to embodiments described above, such as defibrillator 300. It will be recognized that a number of the operations of flowchart 1100 are similar to those of flowchart 1200.

According to an operation 1210, electrical energy is stored, such as in an energy storage module.

According to a next operation 1220, it is determined whether defibrillation is advised for the patient. Execution branches according to the outcome of operation 1220. Operation 1220 can be performed as a result of the analysis of an ECG.

If defibrillation is not advised, execution can return to operation 1210 as shown in the example of FIG. 12, or terminate.

If defibrillation is indeed advised, at operation 1230, a defibrillation shock is delivered to the patient using an ascending waveform. The waveform has a first peak amplitude that is less than a second peak amplitude, such as shown in FIG. 4. As also per the above, the defibrillation shock can be delivered automatically or responsive to a user operating a user interface of the device.

For delivering a shock, the stored energy would be used to charge the capacitor. In most embodiments, the capacitors C1, C2, C3, . . . would be charged only after it has been determined that shock is advised.

For both flowcharts 1100 and 1200, it will be recognized that a number of their operations can be augmented with what was described above.

Notes and Additional/Alternative Implementation Details

In the above description of exemplary implementations, for purposes of explanation, specific numbers, materials configurations, and other details are set forth in order to better explain the present invention, as claimed. However, it will be apparent to one skilled in the art that the claimed invention may be practiced using different details than the exemplary ones described herein. In other instances, well-known features are omitted or simplified to clarify the description of the exemplary implementations.

The inventor intends the described exemplary implementations to be primarily examples. The inventor does not intend these exemplary implementations to limit the scope of the appended claims. Rather, the inventor has contemplated that the claimed invention might also be embodied and implemented in other ways, in conjunction with other present or future technologies.

Moreover, the word "exemplary" is used herein to mean serving as an example, instance, or illustration. Any aspect or design described herein as exemplary is not necessarily to be construed as preferred or advantageous over other aspects or designs. Rather, use of the word "exemplary" is intended to present concepts and techniques in a concrete fashion. The term "technology," for instance, may refer to one or more devices, apparatuses, systems, methods, articles of manufacture, and/or computer-readable instructions as indicated by the context described herein.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

Note that the order in which the processes are described is not intended to be construed as a limitation, and any number of the described process blocks can be combined in any order to implement the processes or an alternate process. Additionally, individual blocks may be deleted from the processes without departing from the spirit and scope of the subject matter described herein.

One or more embodiments described herein may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "computer-readable media" includes computer-storage media. For example, computer-storage media may include, but are not limited to, magnetic storage devices (e.g., hard disk, floppy disk, and magnetic strips), optical disks (e.g., compact disk [CD] and digital versatile disk [DVD]), smart cards, flash memory devices (e.g., thumb drive, stick, key drive, and SD cards), and volatile and nonvolatile memory (e.g., RAM and ROM).

In the claims appended herein, the inventor invokes 35 U.S.C. §112, paragraph 6 only when the words "means for" or "steps for" are used in the claim. If such words are not used in a claim, then the inventor does not intend for the claim to be construed to cover the corresponding structure, material, or acts described herein (and equivalents thereof) in accordance with 35 U.S.C. §112, paragraph 6.

What is claimed is:

1. An external medical device that facilitates delivery of electrical energy to a patient, the external medical device comprising:
    a discharge circuit configured to deliver energy to a patient via electrodes on the patient's skin; and
    an energy storage module, coupled to the discharge circuit, the energy storage module having two or more energy storage capacitors;
    a defibrillation control unit configured to:
        cause the two or more energy storage capacitors to be coupled in a first manner having a first capacitance;
        cause the two or more energy storage capacitors to start discharging, via the discharge circuit, to the patient using the first capacitance; and
        while still discharging to the patient, cause the two or more energy storage capacitors to change from the coupling of the first manner to be coupled in a second manner having a second capacitance, which is different from the first capacitance.

2. An external medical device according to claim 1, wherein the second manner has a second capacitance that is different from the first capacitance.

3. An external medical device according to claim 1, wherein the defibrillation control unit is further configured to adjust the discharge to accommodate an impedance of the patient, where that impedance may be up to 200 ohms.

4. An external medical device according to claim 1, wherein an amount of time spent discharging in at least one manner is dependent on a patient-related parameter.

5. An external medical device according to claim 1, wherein an amount of time spent discharging in at least one manner is dependent on a patient-related parameter and the patient-related parameter is selected from a group consisting of a patient impedance, a patient current, a capacitor voltage, a patient voltage, a rate of change of a capacitor voltage, a rate of change of a patient voltage, a delivered energy, or a delivered charge.

6. An external medical device according to claim 1, wherein an amount of time spent discharging in at least one manner is dependent on a patient-related parameter and the patient-related parameter is measured before the start of the discharge.

7. An external medical device according to claim 3., wherein an amount of time spent discharging in at least one manner is dependent on a patient-related parameter and the patient-related parameter is measured during the discharge.

8. An external medical device according to claim 1, wherein an amount of time spent discharging in at least one manner is dependent on a patient-related parameter and the duration of a phase of the waveform is based on a measurement of the patient at one point in time and the duration of a second phase of the waveform is based on a second measurement of the patient related parameter.

9. An external medical device according to claim 1, wherein an amount of time spent discharging while in the first manner is between 0.1 millisecond and 3.0 milliseconds.

10. An external medical device according to claim 1, wherein the defibrillation control unit controls a single active switch, and wherein the defibrillation control unit is configured to switch from the first manner to the second manner using only the single active switch.

11. An external medical device according to claim 1, wherein the discharge circuit is configured to selectively deliver at least 1.50J to the patient.

12. An external medical device according to claim 1, wherein the discharge circuit is configured to selectively deliver up to 360J to the patient.

13. An external medical device according to claim 1, wherein the energy storage capacitors are configured to store up to 360J.

14. An external medical device according to claim 1, wherein energy is delivered to the patient through an H-bridge circuit.

15. An external medical device according to claim 14, wherein at least some of the components of the H-bridge have a voltage standoff capability of at least 1.5× a voltage rating of the energy storage capacitors.

16. An external medical device in accordance with claim 1, wherein the first manner includes the two or more energy storage capacitors being coupled together in parallel for charging.

17. An external medical device in accordance with claim 1, wherein second manner includes the two or more energy storage capacitors being coupled together in series for discharging.

18. An external medical device in accordance with claim 1, wherein the energy storage module is further configured to discharge in both the first and second manners with the same polarity relative to the patient.

19. An external medical device in accordance with claim 1, wherein the medical device is selected from a group consisting of a monitor-defibrillator, an automated external defibrillator (AED), and a wearable cardiac defibrillator.

20. An external medical device in accordance with claim 1, wherein the energy storage module is further configured to generate a waveform of the energy that the discharge circuit delivers to the patient, the waveform having a set of at least two peaks, wherein a second peak of the set of at least two peaks has a greater magnitude than a first peak of the set of at least two peaks.

21. An external medical device in accordance with claim 1, wherein the energy storage module is further configured to generate a waveform of the energy that the discharge circuit delivers to the patient, the waveform rising rapidly to a first amplitude, decaying exponentially to a second amplitude, rising rapidly to a third amplitude higher than the first and the second amplitude, and decaying exponentially to a fourth amplitude.

22. An external medical device in accordance with claim 1, wherein the energy storage module is further configured to generate a waveform of the energy that the discharge circuit delivers to the patient, the waveform falling rapidly to a first amplitude, increasing exponentially to a second amplitude, falling rapidly to a third amplitude greater than the first and the second amplitude, and increasing exponentially to a fourth amplitude.

23. An external medical device comprising:
an discharge circuit configured to deliver a energy to a patient via electrodes on the patient's skin; and
an energy storage module, coupled to the discharge circuit, the energy storage module being configured to generate a waveform of the energy that the discharge circuit delivers to the patient, the waveform being characterized by a set of at least two peaks, wherein a second peak of the set of at least two peaks has a greater amplitude than a first peak of the set of at least two peaks.

24. An external medical device in accordance with claim 23, wherein the medical device is selected from a group consisting of a monitor-defibrillator, an automated external defibrillator (AED), and a wearable cardiac defibrillator.

25. An external medical device in accordance with claim 23, wherein the
energy storage module is further configured to adjust the waveform to accommodate an impedance of the patient, where that impedance may be up to 200 ohms.

26. An external medical device in accordance with claim 23, wherein the energy storage module is further configured to switch two or more energy storage capacitors from a parallel configuration to a series configuration while the discharge circuit delivers is delivering energy to the patient.

27. An external medical device comprising:
a discharge circuit configured to deliver energy to a patient via electrodes on the patient's skin;
an energy storage module, coupled to the discharge circuit, the energy storage module including two or more energy storage capacitors, the energy storage module being configured to switch the two or more energy storage capacitors from a parallel configuration to a series configuration while the two or more energy storage capacitors are delivering energy to the patient via the discharge circuit.

28. An external medical device in accordance with claim 27, wherein the medical device is selected from a group consisting of a monitor-defibrillator, an automated external defibrillator (AED), or a wearable cardiac defibrillator.

29. An external medical device in accordance with claim 27, wherein the waveform is selected from a group consisting of a biphasic waveform, a sequentially-stepped biphasic waveform, or an ascending amplitude waveform.

30. An external medical device in accordance with claim 27, wherein the energy storage module is further configured to generate a waveform of the energy that the discharge circuit delivers to the patient, the waveform being characterized by a set of at least two peaks, wherein a second peak of the set of at least two peaks has a greater amplitude than a first peak of the set of at least two peaks.

31. An article comprising: a storage medium, the storage medium having instructions stored thereon, wherein when the instructions are executed by at least one medical device configured to deliver electrical energy to a patient, they cause the medical device to perform operations comprising:

delivering energy to a patient via electrodes on the patient's skin and using two or more energy storage capacitors that are coupled together in a first configuration in the medical device; and while delivering the energy to the patient, switching the coupling of the two or more energy storage capacitors from the first configuration to a second configuration.

32. An article of claim 31, wherein:

the first configuration includes the two or more energy storage capacitors being coupled together in a parallel configuration in the medical device; and the second configuration includes the two or more energy storage capacitors being coupled together in a serial configuration in the medical device.

33. A method that facilitates delivery of electrical energy to a patient by an external medical device, the method comprising:

delivering energy to a patient via electrodes on the patient's skin and using two or more energy storage capacitors configured to have a first capacitance configuration; and during delivery of the energy to the patient, switching the configuration of the two or more energy storage capacitors from the first capacitance configuration to a second capacitance configuration, wherein the first capacitance configuration is different from the second capacitance configuration.

34. A method in accordance with claim 33, further comprising generating a waveform of the energy, the waveform including a set of at least two peaks, wherein a second peak of the set of at least two peaks has a greater magnitude than a first peak of the set of at least two peaks.

35. A method in accordance with claim 33, wherein the first capacitance configuration is a parallel configuration and the second capacitance configuration is a series configuration.

* * * * *